US00PP17788P2

(12) United States Plant Patent
Gitzels

(10) Patent No.: US PP17,788 P2
(45) Date of Patent: Jun. 5, 2007

(54) ***DAHLIA* PLANT NAMED 'DAPASULO'**

(50) Latin Name: *Dahlia variabilis*
Varietal Denomination: Dapasulo

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/319,683

(22) Filed: Dec. 28, 2005

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
*Assistant Examiner*—Annette H Para
(74) *Attorney, Agent, or Firm*—Audrey Charles

(57) ABSTRACT

A new and distinct cultivar of *Dahlia* plant named 'Dapasulo' characterized by its red-purple and white-bicolored flowers, medium green-colored foliage, good basal branching character, and moderately vigorous, upright growth habit.

1 Drawing Sheet

Latin name of genus and species of plant claimed: *Dahlia variabilis.*
Variety denomination: 'Dapasulo'.

BACKGROUND OF THE INVENTION

The present invention relates to a new and distinct cultivar of *Dahlia* plant botanically known as *Dahlia variabilis* and hereinafter referred to by the cultivar name 'Dapasulo'.

The new cultivar originated in a controlled breeding program in Rijsenhout, the Netherlands during October 2001. The objective of the breeding program was the development of freely flowering *Dahlia* cultivars with large flowers and a moderately vigorous growth habit.

The new cultivar is a naturally occurring sport of 'Carol', U.S. Plant Pat. No. 6,926 characterized by its dark purple-colored flowers, medium green-colored foliage, and moderately vigorous, upright growth habit. The new cultivar was discovered and selected by the inventor on Oct. 1, 2001 in a controlled environment at Rijsenhout, the Netherlands.

Asexual reproduction of the new cultivar by terminal stem cuttings since October 2001 at Rijsenhout, the Netherlands and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Dapasulo' as a new and distinct cultivar of *Dahlia* plant:

1. Red-purple and white-bicolored flowers;
2. Medium green-colored foliage;
3. Good basal branching character; and
4. Moderately vigorous, upright growth habit.

Plants of the new cultivar differ from plants of the parent primarily in flower color.

Of the many commercially available *Dahlia* cultivars known to the inventor, the most similar in comparison to the new cultivar is 'Dapapu', U.S. Plant Pat. No. 17,127. However, in side by side comparisons, plants of the new cultivar differ from plants of 'Dapapu' in the following characteristics:

1. Plants of the new cultivar are taller than plants of 'Dapapu';
2. Plants of the new cultivar have a less deeply dentate leaf margin than plants of 'Dapapu'; and
3. Plants of the new cultivar have a different flower color from plants of 'Dapapu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Dapasulo'. The plants were grown in 10 cm pots for 8 weeks in a greenhouse at West Chicago, Ill.

DETAILED BOTANICAL DESCRIPTION

Figure 1:
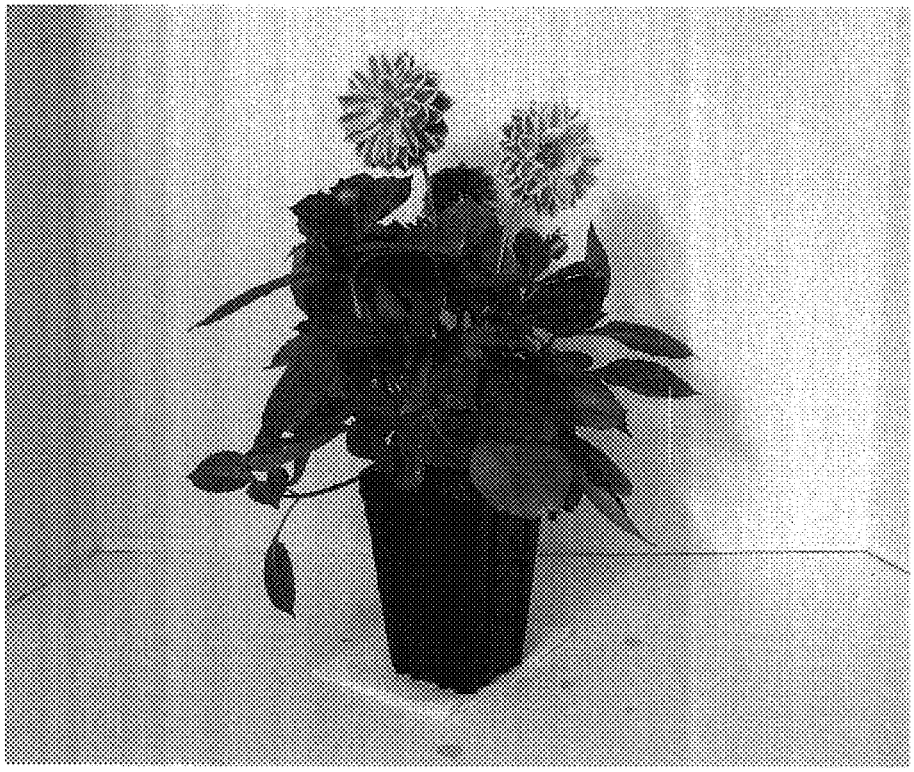
FIG. 1 illustrates a side view of the overall growth and flowering habit of 'Dapasulo'.
Figure 2:
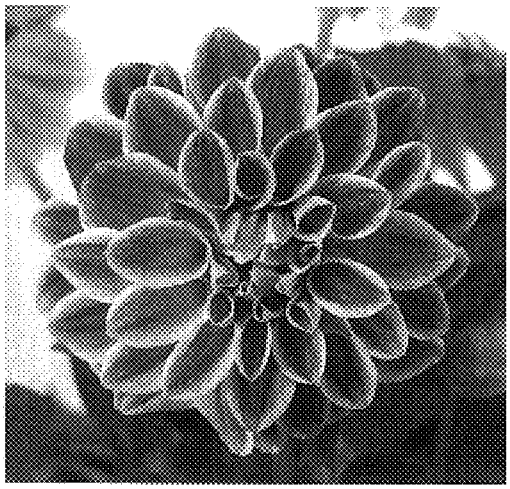
FIG. 2 illustrates a close-up view of a single inflorescence of 'Dapasulo' with most of the ray florets open and the disc florets unopened.
Figure 3:
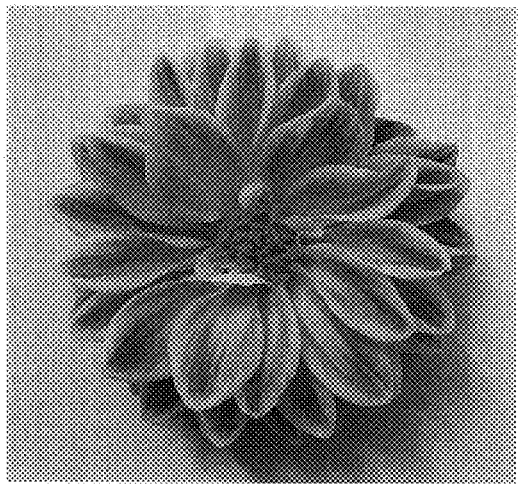
FIG. 3 illustrates a close-up view of the ventral surface of an inflorescence of 'Dapasulo' with fully open ray florets and fully open disc florets.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on December 21 between 10:00 a.m. and 11:00 a.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65° F. to 75° F. (18° C. to 24° C.) during the day and approximately 60° F. to 65° F. (15° C. to 18° C.) during the night. Greenhouse light levels of approximately 4,000 to 6,000 footcandles were maintained during the day.

Botanical classification: *Dahlia variabilis* cultivar Dapasulo.

Parentage:

*Parent.*—*Dahlia variabilis* cultivar Carol, U.S. Plant Pat. No. 6,926.

Propagation:

*Type cutting.*—Terminal stem.

*Time to initiate roots.*—Approximately 7 to 10 days.

*Time to produce a rooted cutting.*—Approximately 21 to 28 days.

*Root description.*—Fine, fibrous.

*Rooting habit.*—Freely branching.

*Tuber formation.*—Will form under short day conditions of at least 13 to 14 hours of darkness.

Plant description:

*Crop time.*—Approximately 6 to 8 weeks from a rooted cutting.

*Growth habit.*—Basal branching; pinching enhances branching.

*General appearance.*—Moderately vigorous, upright.

*Size.*—Height from soil level to top of plant plane: Approximately 26.3 cm. Height from soil level to top of foliage: Approximately 23.3 cm. Width: Approximately 29.1 cm.

*Branch.*—Quantity per plant: 3. Strength: Strong. Length: Approximately 12.3 cm. Diameter: Approximately 6.5 mm. Texture: Glabrous. Color: 144A. Length of central internode: Approximately 1.0 cm.

*Foliage.*—Quantity of leaves per lateral branch: Approximately 15. Type: Simple. Fragrance: None. Arrangement: Opposite. Aspect: Petiole is at an acute angle to stem and mature blade is perpendicular to stem. Shape of leaf: Ovate. Margin of leaf: Widely dentate. Apex of leaf: Acuminate. Base of leaf: Acuminate. Venation pattern: Pinnate.

*Simple leaf.*—Length: Approximately 9.4 cm. Width: Approximately 6.5 cm. Texture of upper and lower surfaces: Sparsely pubescent with denser pubescence along veins. Color of upper surface: Closest to 137A with venation of 144A. Color of lower surface: 191A with venation of 144A. Length of petiole: Approximately 3.5 cm. Diameter of petiole: Approximately 3.5 mm. Texture of upper and lower surfaces of petiole: Glabrous. Color of upper and lower surfaces of petiole: 144A.

Flowering description:

*Flowering habit.*—'Dapasulo' is freely flowering under outdoor growing conditions with substantially continuous blooming from spring through autumn and year round in the greenhouse environment.

*Time to first flower.*—Approximately 11 weeks from sticking of unrooted cutting.

*Lastingness of individual bloom.*—Approximately 4 weeks.

Inflorescence description:

*Appearance.*—Type: Composite. Aspect: Facing outward. Flower arrangement: Terminal, arising from leaf axils on strong peduncles positioned over the foliage. Disc and ray florets arranged acropetally on a capitulum. Persistent.

*Quantity per plant.*—2.

*Fragrance.*—None.

*Shape/size.*—Hemispherical when ray florets are fully open. Inflorescence diameter: Approximately 7.1 cm. Inflorescence depth: Approximately 3.7 cm. Disc diameter: Approximately 9.4 mm. Receptacle diameter: Approximately 1.1 cm. Receptacle depth: Approximately 3.0 mm. Receptacle color: Between 150B and 150C.

*Peduncle.*—Strength: Strong. Aspect: Erect. Length: Approximately 12.4 cm. Diameter: Approximately 3.0 mm. Texture: Glabrous. Color: 144A with an overlay of 183A.

*Bud.*—Rate of bud opening: Generally takes approximately 2 weeks for bud to progress from first color to fully open inflorescence. Shape: Oval. Depth at first color: Approximately 1.7 cm. Diameter at first color: Approximately 1.6 cm. Texture at first color: Glabrous. Color: Outer surface of bract is 150B with 137A at base, petal background is N187D with central stripes of N78A and with 150B at base and 154D at apex.

*Ray florets.*—Quantity per inflorescence: Approximately 65. Arrangement: Imbricate, in several whorls. Aspect: Cupped. Shape: Oblanceolate. Margin: Entire. Apex: Apiculate. Base: Attenuate. Appearance: Dull. Length: Approximately 3.7 cm. Width: Approximately 1.9 cm. Texture of upper and lower surfaces: Glabrous. Color of upper surface when first open: Darker than 63A fading to 63D toward base, 2B at base, and N155B at margins. Color of lower surface when first open: 63A at tip fading to 63D toward base and 2B at base. Color of upper surface when fully open: Background of N155B overlain with streaks of varying amounts of 71A to 71B fading to 71C toward base and 2B at base. Color of lower surface when fully open: Background of N155B overlain with streaks of varying amounts of 71B fading to 71D toward base and 2B at base. Color of upper surface before senescence: 77A at tip fading to 77C toward base and 2B at base. Color of lower surface before senescence: 77B at tip fading to 77D toward base and 2B at base.

*Disc florets.*—Quantity per inflorescence: Approximately 39. Arrangement: Massed in center of inflorescence. Aspect: Erect. Shape: Tubular. Margin: Entire. Apex: 5 acute down turning tips. Base: Fused. Length: Approximately 1.3 cm. Diameter at apex: Approximately 2.5 mm. Diameter at base: Approximately 1.0 mm. Texture: Glabrous. Color when fully open: N144C, translucent.

*Outer involucral bracts.*—Quantity: 8. Aspect: Flat. Shape: Rhombic. Margin: Entire. Apex: Acute. Base: Truncate. Length: Approximately 1.5 cm. Width: Approximately 6.5 mm. Texture of upper and lower surfaces: Glabrous. Color of upper and lower surfaces: 138A.

*Inner involucral bracts.*—Quantity: One per floret. Shape: Linear, slightly overlapping. Margin: Entire. Apex: Broadly acute. Base: Truncate. Length of outermost: Approximately 1.9 cm. Width of outermost: Approximately 5.5 mm. Length of innermost: Approximately 7.3 mm. Width of innermost: Approximately 2.0 mm. Texture of upper and lower surfaces of all bracts: Glabrous. Color of upper and lower surfaces: 150B, translucent with a base of 137A for outermost.

*Reproductive organs.*—Androecium: On disc florets. Stamen quantity: 5. Anther shape: Linear. Anther length: Approximately 4.0 mm. Anther color: 13A. Pollen amount: Abundant. Pollen color: 16A. Gynoecium: On disc and ray florets. Pistil length: Approximately 1.4 cm. Stigma shape: 3 branches. Stigma length: Approximately 3.5 mm. Stigma color: 13A. Style length: Approximately 1.3 cm. Style color: 1D, transparent. Ovary diameter: Approximately 1.0 mm. Ovary color: 1D.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Dapasulo', substantially as herein shown and described.

* * * * *